(12) United States Patent
Van Krieken et al.

(10) Patent No.: US 8,987,510 B2
(45) Date of Patent: Mar. 24, 2015

(54) METHOD FOR REMOVAL OF THE CYCLIC DIESTER OF A 2-HYDROXY ALKANOIC ACID FROM A VAPOR

(75) Inventors: Jan Van Krieken, Gorinchem (NL); Siebe Cornelis De Vos, Arnhem (NL); Johannes Adrianus Kamp, Vlijmen (NL)

(73) Assignee: Purac Biochem BV, Gorinchem (NL)

( * ) Notice: Subject to any disclaimer, the term of this patent is extended or adjusted under 35 U.S.C. 154(b) by 40 days.

(21) Appl. No.: 14/006,728

(22) PCT Filed: Mar. 29, 2012

(86) PCT No.: PCT/EP2012/055706
§ 371 (c)(1),
(2), (4) Date: Sep. 23, 2013

(87) PCT Pub. No.: WO2012/136568
PCT Pub. Date: Oct. 11, 2012

(65) Prior Publication Data
US 2014/0012043 A1    Jan. 9, 2014

Related U.S. Application Data

(60) Provisional application No. 61/471,925, filed on Apr. 5, 2011.

(30) Foreign Application Priority Data

Apr. 5, 2011  (EP) ..................................... 11161172

(51) Int. Cl.
C07C 51/42     (2006.01)
C07C 319/12    (2006.01)
B01D 3/00      (2006.01)
C07D 319/12    (2006.01)

(52) U.S. Cl.
CPC ................ C07C 51/42 (2013.01); B01D 3/008 (2013.01); C07D 319/12 (2013.01)
USPC .......................................... 562/589; 562/580

(58) Field of Classification Search
None
See application file for complete search history.

(56) References Cited

U.S. PATENT DOCUMENTS

2010/0252076 A1   10/2010   Hagen et al.

FOREIGN PATENT DOCUMENTS

EP    2 128 184 A1    12/2009
JP    A 10-17653      1/1998

OTHER PUBLICATIONS

Translation of Nov. 4, 2014 Office Action issued in Chinese Patent Application No. 201280016694.7.
Xiaoyan et al.; "Preparation and degradation of polylactide and its copolymer;" Journal of Beijing University of Chemical Technology; Feb. 29, 2004; vol. 31; No. 1; pp. 51-56 (with abstract).
Bergmann et al; "Note on the Preparation of Cyclohexen-1-aldehyde;" Journal of Organic Chemistry; 1958; vol. 23; No. 10; pp. 1553-1554.
May 4, 2012 Search Report issued in International Patent Application No. PCT/EP2012/055706.
May 4, 2012 Written Opinion issued in International Patent Application No. PCT/EP2012/055706.

*Primary Examiner* — Yevegeny Valenrod
(74) *Attorney, Agent, or Firm* — Oliff PLC

(57) ABSTRACT

The invention relates to a method for the removal of the cyclic diester of a 2-hydroxy alkanoic acid from a vapor containing said diester, wherein the vapor is contacted with an aqueous solution so that the diester dissolves in said solution. According to the invention, the method is characterized in that the solution is an alkaline solution, preferably having a pH above 10. The problem of the formation of slurries of the diester in the aqueous solutions can be prevented by the present invention. The method can be applied with great advantage in the production or conversion of lactide.

13 Claims, 1 Drawing Sheet

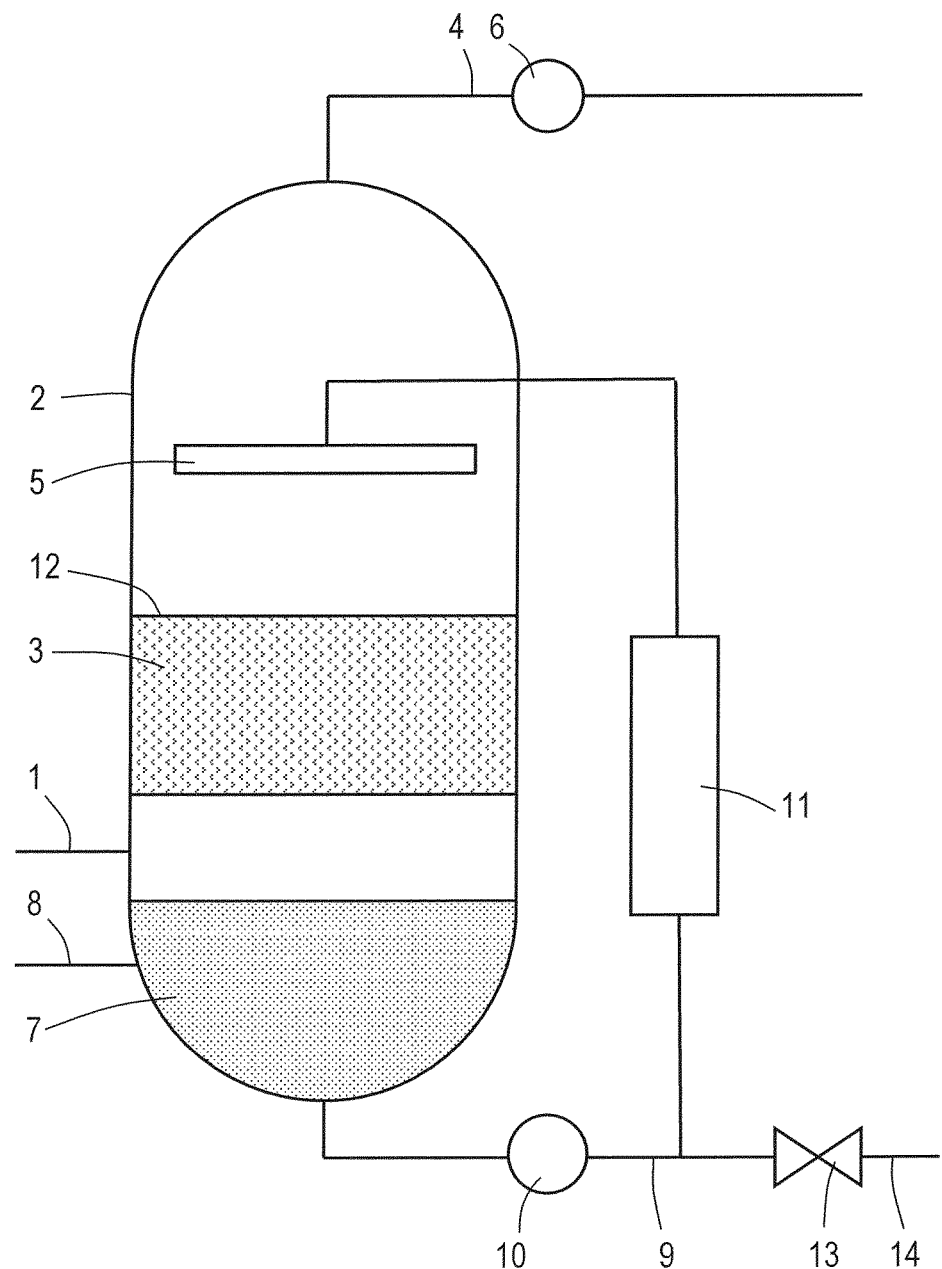

METHOD FOR REMOVAL OF THE CYCLIC DIESTER OF A 2-HYDROXY ALKANOIC ACID FROM A VAPOR

The invention relates to a method for the removal of the cyclic diester of a 2-hydroxy alkanoic acid from a vapor containing said diester, wherein the vapor is contacted with an aqueous solution so that the diester dissolves in said solution.

2-Hydroxy alkanoic acids and their cyclic diesters currently receive much attention. These acids and diesters can be used in the production of polymers of the type poly(2-hydroxy alkanoic) acids. A well-known example of such polymers is polyglycolide. Most attention however is devoted to polylactide (also referred to as polylactic acid and abbreviated as PLA). This is an aliphatic polyester, which can be manufactured from renewable resources. Such manufacture may include the bacterial fermentation of natural occurring resources like starch or other carbohydrates into lactic acid. PLA is usually synthesized by ring-opening polymerization (ROP) of lactide, the cyclic diester (or cyclic dimer) of lactic acid (2-hydroxy propanoic acid).

Both in the synthesis of the cyclic diesters as well as in their conversion into the polymer, vapor streams comprising small amounts of the cyclic diester have to be removed. To reduce losses, the amount of cyclic diester in such vapors should be minimal. Moreover, the hydrolysis products of such diesters can cause corrosion problems in the apparatus used for the synthesis or conversion of these diesters. This holds especially for lactic acid, the hydrolysis product of lactide. Special condensing and washing methods have been developed in order to lower the diester amounts in exhausted vapors as much as possible.

A method as mentioned in the opening paragraph has been described in the Japanese patent application with publication number JP 10-17653. More specifically, this document describes a method for the production of PLA from lactide in a polymerization reaction vessel. In this method, unreacted lactide is removed as a vapor from the reaction vessel, which vapor is substantially liquefied in a heat exchanger and subsequently collected in a drain pot. The small part of the lactide which is not liquefied is transported by means of an ejector mechanism to a barometric condenser. In this condenser, the lactide is contacted with an aqueous solution, which mainly contains lactide, its hydrolysis product lactic acid and water.

In practice the known method has a clear disadvantage. The relatively slow hydrolysis of lactide into lactic acid in an aqueous solution combined with the low solubility of lactide in aqueous solutions, can lead to the formation of lactide slurries in such solutions. This is especially the case when the equipment is operated at low pressure. In these circumstances, the working temperature should be chosen relatively low to avoid boiling of the aqueous solution. A low working temperature results in a low hydrolysis rate. According to the Japanese patent application, special filters have been applied in one of the condenser constructions to filter the lactide slurry. In this manner, clogging of various apparatus parts of the condenser construction by the lactide slurry is prevented. Introducing additional filters in the condenser construction however cause an undesired increase of the apparatus costs.

The present invention aims at improving the known method. In particular, the invention has the purpose to provide an alternative method which preferably can be performed with higher efficiency, simpler equipment and/or at lower costs.

These and other objects of the invention are achieved by means of a method for the removal of a cyclic diester of a 2-hydroxy alkanoic acid from a vapor containing said diester, wherein the vapor is contacted with an aqueous solution so that the diester dissolves in said solution, which method is further characterized in that the solution is an alkaline solution. By definition, such solution has a pH (acidity degree) above 7.

The invention is based on the insight gained by the inventors that the hydrolysis of cyclic diesters of 2-hydroxy alkanoic acids in an aqueous solution can be highly accelerated if the hydrolysis is performed in an alkaline solution. Due to the hydrolysis of these diesters in water, the acidity of such aqueous solution increases. This is especially the case in non-buffered solutions. Hydrolysis of a cyclic dimer molecule results in the formation of one molecule of its corresponding linear dimer or two molecules of its corresponding 2-hydroxy alkanoic acid monomers. Formation of these hydrolysis products results in a drop of the pH of the solution to values far below 7. Under acidic conditions, the hydrolysis of the mentioned diesters appears to proceed relatively slow. Under alkaline conditions however, a much quicker hydrolysis appears to happen. Due to the described quicker hydrolysis under alkaline conditions, the problem of formation of lactide slurry as described for the prior art process is largely diminished and, if conditions are well-chosen, does even not occur at all.

It is stressed that the lactide-containing vapor or gas may comprise additional components. Depending of the process from which the vapor is drawn, the vapor may also contain hydrolysis products of the cyclic diester, water and/or other components that originate from the method as well as leakage gas from the surroundings. Such hydrolysis products of the cyclic dimer may be the corresponding linear dimer or the corresponding 2-hydroxy alkanoic acid monomer.

An interesting embodiment of the presently invented method is characterized in that that the diester is lactide and the 2-hydroxy alkanoic acid is lactic acid. Experiments have shown that the rate of the hydrolysis of lactide into lactic acid is strongly enhanced if the hydrolysis proceeds in an aqueous solution with a pH above 7. This elevated pH induces the lactic acid to be predominantly in its lactate form. The counter ion for of lactate molecule depends on the nature of the base used for the actual alkalization.

It is noted that this hydrolysis effect is not limited to a special type of lactide. Caused by the presence of two asymmetric atoms in lactide, this molecule can exist in three geometrically different structures, which have a diastereomeric relationship. These different structures can be distinguished as (R,R)-lactide (or D-lactide), (S,S)-lactide (or L-lactide) and (R,S)-lactide (or meso-lactide). All three lactide diastereomers show the effect of an increased hydrolysis rate under alkaline conditions.

A preferred embodiment of the invented method has the feature that the pH of the solution is maintained above 10. Under this condition, hydrolysis of the cyclic diester occurs almost exclusively via a process which is called 'saponification'. The mechanism underlying this alkaline hydrolysis is responsible for the quick decomposition of the diester into the corresponding linear dimer. Under these circumstances, scission of the ester bond produces an alcohol together with a salt of a carboxylic acid. In this particular case, the alcohol and the deprotonated carboxylic acid are parts of the same molecule (such as f.e. lactate). Contrary to acidic hydrolysis, alkaline hydrolysis is not an equilibrium reaction, but a reaction which proceeds to 100% conversion. This mechanism of hydrolysis therefore differs completely from the mechanism responsible for hydrolysis under acidic conditions. When the pH of the solution is kept above 10, no lactide slurries are observed. Under these circumstances measures for filtering lactide slurries are not needed and a more reliable operation of the method is achieved. Preferably the pH of the aqueous solution is kept above 11. Under these conditions, the ester hydrolysis rate is considerably accelerated. The hydrolysis rate of cyclic diesters, and especially of lactide, is even further enhanced when the pH of the aqueous solution is above 12.

A further interesting embodiment of the method according to the invention has the feature that the pH of the alkaline solution is maintained in a desired range by adding a base. Different types of bases can be used for this purpose, such as Lewis bases (like pyridine) or Brønsted bases (like liquid ammonia). Application of cheaper metal oxides or metal carbonates provides better results. Simple hydroxides, like ammonium hydroxide are preferred over the before-mentioned bases. Even better results are achieved when a metal hydroxide is used as the base, of which sodium hydroxide and potassium hydroxide are the bases of first choice. The bases are preferably used as concentrated aqueous solutions. In this form, they can be very accurately and easily added to the alkaline solution in which the hydrolysis occurs. Such concentrated solutions may contain approximately 30-55 w/w-% of the specific base in water. Sodium hydroxide and potassium hydroxide cause lactic acid formed during the hydrolysis of lactide to convert into sodium lactate and potassium lactate, respectively. Generally speaking, lactate salts show a good solubility in aqueous solutions. This holds especially for the Na- and the K-salt of lactic acid.

Advantageous is also the embodiment of the invented method in which the base is continuously added. Such embodiment can be efficiently used in continuous production processes in which a cyclic diester, such as lactide, is continuously removed from a vapor stream or a gas stream containing such diester.

Much attention is also devoted to the embodiment of the invented method having the feature that the amount of the base added to the solution is automatically controlled based on the value of the pH of the solution. In this embodiment of the invention, the supply of base to the aqueous solution is adjusted by means of a feed-back mechanism in which the pH of the solution provides an input value. Such embodiment can be very relevant for implementation in continuous production processes.

Special practical relevance provides the embodiment of the invented method in which the temperature of the solution is kept in the range between 5° C. and 40° C. Practice has shown that under atmospheric conditions, the method according to the invention can be performed at any temperature between the freezing point and the boiling point of the aqueous solution. In practice this means any temperature between approximately −20° C. and 110° C. However, many of the processes in which cyclic diester-containing vapors are removed and cleaned from a vapor are performed at low pressures, which are often in the range between 1 and 40 mbar and especially between 2 and 25 mbar. Under these conditions, the process works optimal in temperature ranges between 5° C. and 40° C. and preferably between 10° C. and 25° C.

Interestingly, it was found that the invented process can be performed at lower pressures than the prior art process. Thus, when aqueous solutions with the same concentration of lactic acid and lactate salts are compared under identical pressure conditions, the boiling point of the latter type solutions appear to be significant higher. The fact that the process can be executed at a lower pressure before the aqueous solution starts to boil offers an important advantage.

Another very practical embodiment of the invented method has the feature that the vapor and the solution are contacted in a column, whereby a stream of the vapor and a stream of the solution are guided in opposite directions through said column. In this counter-current configuration of the invented method, a very intimate contact between the vapor and the aqueous solution can be realized as a result of the counter flow of the vapor and the solution. Especially this embodiment of the presently invented method can be applied with great success under low pressure conditions.

A further improvement of the before-mentioned embodiment of the invented method is achieved if the solution is sprinkled in said column by means of a liquid distributor. With such liquid distributor droplets of the aqueous solution are formed in the column. The formation of droplets in the column increases the liquid-vapor interfacial area, resulting in a better mass transfer between the liquid and the vapor. This results in a more efficient removal of the cyclic diester (especially in the form of lactide) from the vapor stream. As no slurry of cyclic diester is formed in the liquid, no clogging of the liquid distributor is observed. Therefore, liquid distributors with very small liquid openings can be used in these circumstances.

Another improvement of the invented method is achieved if the solution and the vapor are guided through a packed bed, which is present in the column. The presence of such packed bed further enhances the vapor-liquid interfacial area. Under these circumstances, the mass transfer rate of the cyclic diester such as lactide from the vapor into the liquid is strongly enhanced. As the aqueous solution is alkaline, no clogging of the packed bed due to non-dissolved cyclic diester will occur. It is noted that different types of packed beds, such as stacked and random packing can be used within the concept of the present invention. The random packing may contain rings or saddles.

A further embodiment of the method according to the present invention is characterized in that the solution is circulated. As the aqueous solution is maintained at a pH above 7 and preferably above 10, cyclic diesters formed of any 2-hydroxy alkanoic acid are caused to hydrolyze rapidly into substantially a salt of the corresponding 2-hydroxy alkanoic acid. Such hydrolysis products appear to dissolve readily in the alkaline aqueous solution. As a consequence of the rapid diester hydrolysis and the high solubility of the corresponding salts, only a relatively small amount of such alkaline solution is needed during the washing process. So, the dimensions of the stock of alkaline solution in the apparatus can be relatively small, leading to a lowering of the costs of the whole apparatus.

Also interesting is the embodiment of the method pursuant to the present invention having the feature that the circulating solution is guided through a heat exchanger. This embodiment is especially useful in case that the vapor containing the cyclic diester has a rather high temperature. This means a temperature in the range between 95° C. and 250° C. In such situation, the temperature of the aqueous solution may raise rather quickly. As the invented method is preferably used in processes under low pressure conditions, this is highly undesired. So, premature boiling of the heated solution may be the undesired result, especially when the washing liquid is circulating. The presence of a heat exchanger can prevent this problem by absorbing a part of the thermal energy of the aqueous solution.

These and other aspects of the invention will be apparent from and elucidated with reference to the experiments described hereinafter and to the drawing, in which, FIG. 1 shows in cross section a device in which the method can be performed.

It is stressed that the FIGURE is schematic and not to scale.

In a first experiment according to the invention, a vapor which contains lactide (i.e. the dehydrated cyclic diester of lactic acid or 2-hydroxy propanoic acid) is guided via vapor inlet pipeline 1 into wet washing column 2 shown in FIG. 1. Said vapor may originate from a process in which lactide is manufactured or in which polylactic acid (PLA) is manufactured. Column 2 comprises packed bed 3, which extends over the whole internal diameter of the column. The column is further equipped with a vapor outlet pipeline 4 and a liquid distributor 5. The vapor travels through packed bed 3 and exits the column via vapor outlet pipeline 4. With vacuum pump 6, a reduced pressure of approximately 15 mbar is created in the column. Pump 6 further sucks the vapor containing the cyclic diester, such as lactide, from inlet pipeline 1, through column 2, packed bed 3 and outlet line 4 to an exhaust collection system (not shown).

Column 2 further comprises a liquid storage compartment 7, which contains an aqueous solution. Additional liquid can be introduced in compartment 7 via liquid inlet pipeline 8. In this experiment according to the invention, the aqueous solution in compartment 7 has been made an alkaline solution by adding a base. This solution is circulated through a liquid circulation system comprising liquid circulation pipeline 9, which circulation is powered by liquid pump 10. In practice, the aqueous solution is pumped from the liquid storage compartment 7 via pipeline 9 and heat exchanger 11 to liquid distributor 5. In distributor 5, the alkaline solution is converted from a liquid stream into small droplets. These droplets fall onto and distribute over the upper surface 12 of packed bed 3. Due to gravity, the droplets of the aqueous solution travel through packed bed 3 and fall in the aqueous solution present in storage compartment 7. The size of compartment 7 depends on residence time required under the operation conditions used. It is noted that for the present invention, it is not essential that compartment 7 is integrated in column 2 as shown in the present embodiment.

Due to the presence of packed bed 3, an efficient mass transfer of the cyclic diester of the 2-hydroxy alkanoic acid (here: lactide) from the vapor into the aqueous solution can be realized. Accordingly, the lactide is washed out from the vapor into the aqueous solution. Possible heat entered into the column by means of the vapor stream will be efficiently transferred into the alkaline aqueous solution and can subsequently be removed from this solution by means of heat exchanger 11.

During the whole experiment, the pH of the solution was maintained above 10. This was achieved by the addition of a base. In the present experiment, sodium hydroxide was used as the base. It appeared to be advantageous to add the base continuously, preferably in liquid form. For this experiment, a commercially available stock solution of 50 w/w-% of NaOH in water (Brenntag, technical grade) was used. The addition of the hydroxide to the aqueous solution can in principle be realized via any inlet pipeline that enters the circulation system.

Some trial experiments performed with an alkaline aqueous solution having a pH value between 7 and 10 showed that formation of small lactide precipitates can occur under these conditions. The amount of such precipitates decreases however with increasing pH (in the range between pH 7 and pH 10). Above pH 10 no lactide precipitates have been observed. Such precipitates or slurries remained absent even after prolonged contacting the lactide-containing vapor with the circulating alkaline washing solution. During this prolonged circulation, the concentration of sodium lactate in the aqueous solution strongly increased. Due to the high solubility of sodium lactate (>70 w/w. % at 20° C.), this high concentration did not cause any problems, as no slurries were formed.

During the experiment, the pH value of the aqueous solution as a function of time was monitored continuously via a pH sensor (not shown) which was present in liquid circulation pipeline 9. Based on changes of the pH value measured in time, the amount of added base was automatically adjusted via a feed-back mechanism (also not shown) in order to keep the pH of the solution at a constant value. In view of the reduced pressure in column 2, the temperature of the aqueous solution is kept preferably below 40° C. by means of heat exchanger 11. In the present experiment according to the invention, the temperature of the aqueous solution was maintained around 15° C.

The volume of liquid storage compartment 7 of the alkaline solution will increase if additional liquid is entered in the column. In principle, there are two manners which can cause such increase. First, a steam injector (not shown) may be attached to vapor inlet pipe line 1. Such ejector will cause that the vapor entering condenser 2 will contain lactide, water and hydrolysis products of lactide. Secondly, the addition of concentrated base via liquid inlet pipe line 8 into compartment 7 also leads to an increase of the volume of the aqueous solution in compartment 7. However, said volume is preferably kept almost constant. This is achieved by a level-measuring sensor (not shown), which provides data to valve 13 in outlet pipeline 14. If the level of the alkaline solution becomes too high, the level-measuring sensor sends a signal to open said valve 13. Accordingly a desired volume of solution is removed via pipe line 14 until the required volume level of the solution in compartment 7 is reached. The required volume corresponds with the desired level of the solution in compartment 7.

In a comparative experiment not according to the present invention, the starting alkaline solution stock used in the above-described experiment according to the invention is replaced by an aqueous solution having a pH of approximately 7. During circulation of the aqueous solution, it is contacted in packed bed 3 with the lactide-containing vapor stream. Due to hydrolysis, part of the lactide dissolved in the aqueous solution is converted via a linear dimer into lactic acid. As a result, the pH of the aqueous solution drops from pH 7 (of the substantially pure water) to values below pH 4. Depending on the amount of lactide washed out in the aqueous solution, part of the dissolved lactide precipitates in the aqueous solution. These precipitates can clog packed bed 3 or parts from the circulation system (like the liquid distributor 5). This is highly undesired.

In additional experiments according to the present invention, the lactide was replaced by mandelide, the cyclic diester of 2-hydroxy-2-phenylacetic acid (also known as mandelic acid). The solubility behavior of mandelide in a neutral solution, an acid solution and an alkaline solution has been monitored and mutually compared. For this purpose, the acid aqueous solution was made by dissolving 10% by weight of mandelic acid in water. An alkaline aqueous solution was made by adding NaOH until a pH of 13 was reached. The neutral aqueous solution consisted of pure, non-buffered water. To these three aqueous solutions, an amount of 2% by weight of mandelide was added. All solutions were kept at 20° C. and stirred for several hours. In this period of time, the solubility behavior of the mandelide in the aqueous solutions was followed by visual inspection.

It appeared that after 60 minutes, the mandelide had not been dissolved at all in the neutral solution. It further appeared that in the acid solution, almost all of the added mandelide was still not dissolved after said 60 minutes. However, it appeared that in the alkaline solution approximately 50% of the added mandelide was dissolved after 60 minutes.

From these observations, it was concluded that the hydrolysis of mandelide is low in a neutral aqueous solution, slightly better in an acid aqueous solution and by far the best in an alkaline aqueous solution. It is believed that the relatively rapid dissolution of the mandelide in the alkaline aqueous solution is based on the same type of saponification process which is responsible for the rapid hydrolysis of lactide under alkaline conditions. Comparison between the hydrolysis of lactide and mandelide shows that under the same conditions (pH, temperature, concentration), lactide hydrolyses quicker in an alkaline solution than mandelide.

In summary, the method according to the present invention provides an improved method for washing cyclic diesters like lactide from a vapor stream, while clogging problems during the washing process are prevented. Such a method can be used with great advantage in processes that require the removal of lactide or other cyclic 2-hydroxy alkanoic acid dimer from a vapor stream containing such dimer. This is the case during production or such cyclic dimer as well as during or after the use of such dimer in a polymerization process.

While the invention has been illustrated and described in detail in the foregoing description, such description is to be considered illustrative or exemplary and not restrictive; the invention is not limited to the disclosed embodiments and experiments. Variations to the disclosed embodiments can be understood and effected by those skilled in the art in practicing the claimed invention, from a study of the disclosure and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. Method for the removal of the cyclic diester of a 2-hydroxy alkanoic acid from a vapor containing said diester, comprising contacting the vapor with an aqueous solution so that the diester dissolves in said solution, wherein the solution is an alkaline solution.

2. Method according to claim 1, wherein the diester is lactide and the hydroxyl alkanoic acid is lactic acid.

3. Method according to claim 1, wherein the pH of the solution is maintained above 10.

4. Method according to claim 1, wherein the pH of the alkaline solution is maintained in a desired pH range by adding a base.

5. Method according to claim 4, wherein the base is a metal hydroxide.

6. Method according to claim 4, wherein the base is added continuously.

7. Method according to claim 4, wherein the amount of the base which is added to the solution is automatically controlled based on the value of the pH of the solution.

8. Method according to claim 1, wherein the temperature of the solution is kept in the range between 5° C. and 40° C.

9. Method according to claim 1, wherein the vapor and the solution are contacted in a column, whereby a stream of the vapor and a stream of the solution are guided in opposite directions through said column.

10. Method according to claim 9, wherein the solution is sprinkled in said column by means of a liquid distributor.

11. Method according to claim 9, wherein the solution and the vapor are guided through a packed bed, which is present in the column.

12. Method according to claim 9, wherein the solution is circulated.

13. Method according to claim 12, wherein the circulating solution is guided through a heat exchanger.

* * * * *